United States Patent [19]
Schmidt et al.

[11] Patent Number: 5,408,873
[45] Date of Patent: Apr. 25, 1995

[54] FOOT FORCE SENSOR

[75] Inventors: Robert N. Schmidt; Howard J. Chizeck; Richard S. Diefes, all of Cleveland, Ohio

[73] Assignee: Cleveland Medical Devices, Inc., Cleveland, Ohio

[21] Appl. No.: 279,515

[22] Filed: Jul. 25, 1994

[51] Int. Cl.$^6$ ............................................. G01L 1/00
[52] U.S. Cl. ................... 73/862.625; 128/779
[58] Field of Search ..................... 73/862.046, 862.637, 73/862.68, 172, 862.625; 128/774, 779; 345/174

[56] References Cited

U.S. PATENT DOCUMENTS

| | | |
|---|---|---|
| 4,426,884 | 1/1984 | Polchaninoff . |
| 4,503,705 | 3/1985 | Polchaninoff .................. 73/172 |
| 4,644,101 | 2/1987 | Jin et al. . |
| 4,745,930 | 5/1988 | Gonfer . |
| 5,033,291 | 7/1991 | Podoloff et al. . |
| 5,253,654 | 10/1993 | Thomas et al. .................. 128/779 |

FOREIGN PATENT DOCUMENTS

| | | |
|---|---|---|
| 0001574 | 3/1987 | WIPO ................. 128/779 |

OTHER PUBLICATIONS

H. J. Chizeck, et al, A Foot Pressure Sensor for Use in Lower Extremity Neuroprosthetic Development, RESNA 8th Annual Conference, 1985.
Jacqueline J. Wertsch, et al, A Portable Insole Plantar Pressure Measurement System, Journal of Rehabilitation Research and Development, vol. 29, No. 1, 1992.

Primary Examiner—Richard E. Chilcot, Jr.
Assistant Examiner—R. Biegel
Attorney, Agent, or Firm—Robert N. Schmidt; John Henry Vynalek

[57] ABSTRACT

Foot force sensor for measuring compressive force exerted by a foot. The foot force sensor is in the form of an insole made of layers of relatively thin, planar, flexible, resilient, dielectric material. Electrical contact means having first and second poles and electrical leads extending therefrom is interposed between the layers of the insole. An electrically resistive material is also interposed between the layers of the insole but displaced from the electrical contact means. An electrically conductive interconnecting means is connected between the electrical contact means and the electrically resistive material. The electrically conductive interconnecting means has a plurality of electrically isolated conductive paths laterally displaced from one another and extending through it. The electrically conductive interconnecting means has an electrical resistance which decreases as a compressive force applied to it increases, whereby a closed electrical circuit with shear and hysteresis effects reduced by at least about 20% and with resistance varying with the amount of compressive force applied to the insole is established between the first pole and the second pole of the electrical contact means through the electrically conductive interconnecting means and the electrically resistive material.

18 Claims, 2 Drawing Sheets

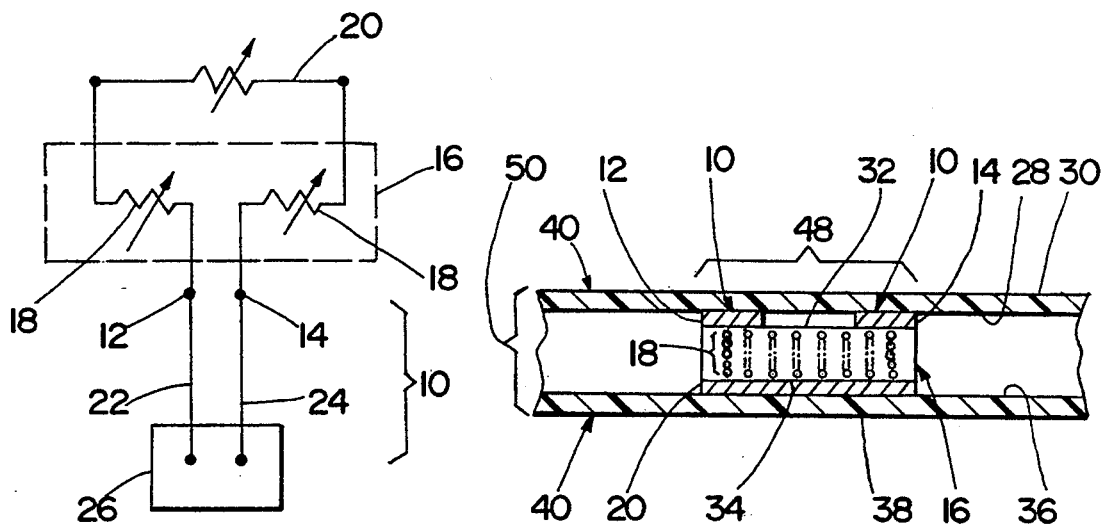
*Fig. 1*  *Fig. 2*
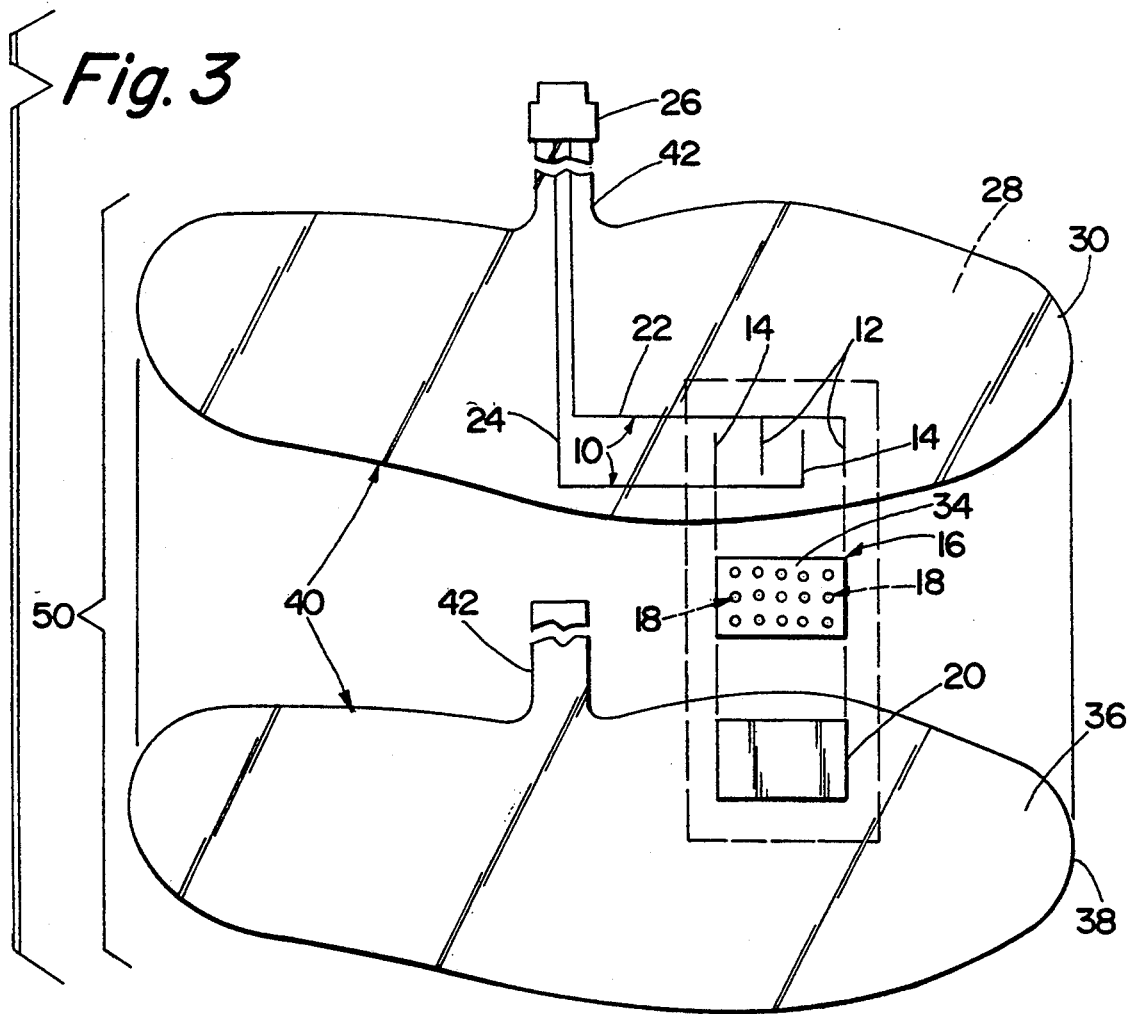
*Fig. 3*

FOOT FORCE SENSOR

This invention was made as a result of work under Contract No. IR43 NS30279-01/02 between U.S. Department of Health and Human Services and Cleveland Medical Devices, Inc. and the U.S. Government has rights in this invention pursuant thereto.

BACKGROUND OF THE INVENTION

The present invention relates to a foot force sensing insole worn inside of a person's shoe and capable of sensing varying compressive force exerted by a person's foot at different points along the foot and transducing the compressive force into electrical signals suitable for transmission to computerized processes, monitoring and analyzing systems for detection, diagnosis, characterization, gait analysis, feedback for automatic control of electrical stimulation devices and substitute sensory feedback.

Individuals with impaired functions of the lower extremity are limited in their abilities to stand, to negotiate curbing and stairs, and to walk. These disabilities often reduce physical access to certain locations, restrict employment opportunities and lower the quality of life. Functional electrical stimulation (FES) technology used alone or in conjunction with orthoses (bracing) provides selective electrical stimulation of nerves and/or muscle allowing some of the above mentioned individuals to stand, walk, maneuver and climb stairs. However, current lower extremity FES systems do not have a sufficient artificial sensory feedback to allow detection of time of foot strike, total force, or center of pressure (center of compressive force) or changes thereto. Essential to the successful and practical application of such systems is an economical, easy to use, reliable, accurate, highly mobile and unobtrusive sensory device which provides a neuroprosthetic sensory input. It is imperative for applications involving insensate feet that the device not only be very thin, lightweight, and allow for mobility; but also be able to detect small changes in the amount of compressive force exerted by the foot on a continuous basis.

There are a number of insole foot force sensing devices currently used for measuring force on the foot. For example, U.S. Pat. No. 4,745,930 discloses a flexible force sensing insole which incorporates multiple electrical switches which close after a certain threshold level of force is imposed on the insole. U.S. Pat. No. 5,033,291 discloses a force sensing device which utilizes a plurality of intersecting electrodes. The electrodes act as open circuit switches at each intersection which close when force is applied to the insole at that intersection location. The resistance between the two electrodes varies with the amount of force applied. U.S. Pat. No. 4,426,884 discloses a flexible force sensor which acts as an open circuit, closing with the application of force on the sensor and having resistance that varies with the amount of force.

While these devices maybe useful in systems used for testing, monitoring and analyzing a person's gait, particularly in laboratory environments, they were not designed as a neuroprosthetic sensory input. Accordingly, a need exists for a foot force sensor which allows for effective application with neuroprosthetic systems.

SUMMARY OF THE INVENTION

The present invention provides a foot force sensor designed to satisfy the aforementioned need. The invention embodies a design which allows for the practical and comfortable mobility of the wearer while providing an electrical signal which varies with the amount of compressive force exerted by the wearer's foot and can be used as a neuroprosthetic sensory input.

Accordingly, the present invention relates to a foot force sensor comprising an insole having a plurality of layers of relatively thin, planar, flexible, resilient, dielectric material and electrical contact means attached to the insole; the electrical contact means having first and second poles and electrical leads extending from the first and second poles; electrically resistive material applied to the insole such that the electrically resistive material is displaced from the electrical contact means; electrically conductive interconnecting means having first and second faces, the first face electrically connected to the electrical contact means and the second face electrically connected to the electrically resistive material, the electrically conductive interconnecting means having a plurality of electrically isolated conductive paths laterally displaced from one another and extending from the first face to the second face, the conductive paths having an electrical resistance which decreases as a compressive force applied to the first or second face increases whereby a closed electrical circuit, with shear and hysteresis effects reduced by at least about 20% and with resistance varying with the amount of compressive force applied to the insole is established between the first pole and the second pole of the electrical contact means through the electrically conductive interconnecting means and the electrically resistive material.

BRIEF DESCRIPTION OF THE DRAWINGS

Further features of the present invention will become apparent to those skilled in the art to which the present invention relates from reading the following specification with reference to the accompanying drawings in which:

FIG. 1 is a schematic diagram illustrating the electrical connections of a foot force sensor.

FIG. 2 is a cross sectional view showing the physical relationship of electrical contact means, electrically conductive interconnecting means and electrically resistive material with the insole.

FIG. 3 is a partial, representative, exploded view of the preferred embodiment of the foot force sensor.

DESCRIPTION OF THE PREFERRED EMBODIMENT

Figure 4:
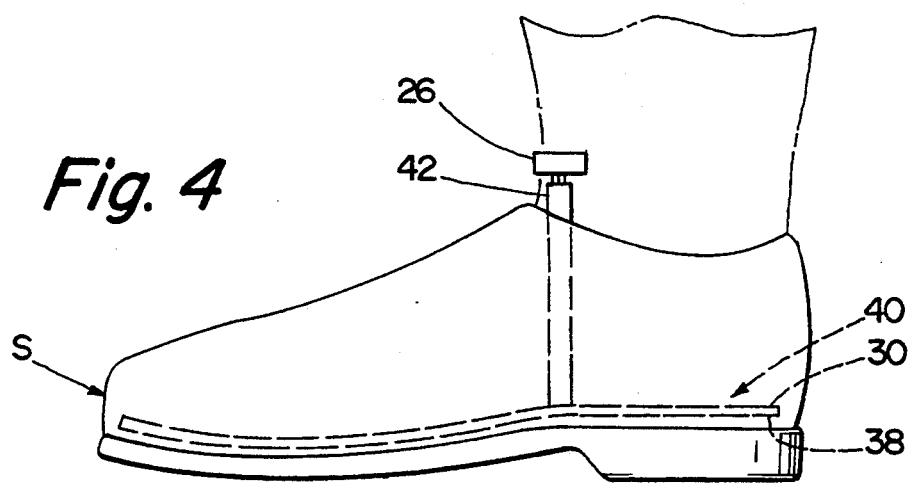
FIG. 4 is a view of a foot in a shoe showing the positioning of the foot force sensor in the shoe, the electrical leads, the connector tab and the terminal connector.

While in the preferred embodiment an environment involving a shoe is used, it is understood that the present invention can be used with any other environment involving the use of a foot force sensor. Referring now to the drawings and more particularly FIG. 1, there is first shown a schematic diagram of the electrical connections of the preferred embodiment. The electrical contact means 10, through its first pole 12 and second pole 14, is connected to the electrically conductive interconnecting means 16. First pole 12 and second pole 14 are independently connected to separate, electrically isolated conductive paths 18 contained within the electrically conductive interconnecting means 16. Each electrically isolated conductive path 18 is connected to the electrically resistive material 20. The electrically resistive material 20 is displaced from the electrical contact means 10 so that the only electrical contact between the electrically resistive material 20 and the electrical contact means 10 is through the electrically conductive interconnecting means 16. As compressive force applied to the electrically conductive interconnecting means 16 increases, its resistance decreases. By exerting more compressive force on the electrically conductive interconnecting means 16, more surface contact is made with the electrically resistive material 20 and the electrical contact means 10 resulting in an electrical path of decreasing resistance. Electrical leads 22, 24 connect the first pole 12 and second pole 14, respectively, to the terminal connector 26. The electrical contact means 10 and electrically resistive material 20 are attached and applied, respectively, to an insole 40 composed of relatively thin, planar, flexible, resilient, dielectric material (not shown).

Referring now to FIG. 2, a cross sectional view of the physical relationships of the preferred embodiment of a foot force sensor is shown. The insole 40 has a plurality of layers of relatively thin, flexible, planar, resilient, dielectric material, in the preferred embodiment shown as first layer 30 and second layer 38. It is understood, though, that additional layers may be utilized, especially to provide spacing and electrical insulation between the electrical contact means 10 and the electrically resistive material 20. The first layer 30 and the second layer 38 are juxtaposed to one another in a face-to-face stacked relationship. The electrically resistive material 20 and electrical contact means 10 are interposed between the first layer 30 and second layer 38 in a manner so that the electrical contact means 10 and the electrically resistive material 20 are displaced from one another and not in direct physical contact. The electrical contact means 10 and the electrically resistive material 20 are in direct, intimate contact with the electrically conductive interconnecting means 16 such that the electrical contact means 10 and electrically resistive material 20 are electrically insulated from one another except for the electrical contact with and through the electrically conductive interconnecting means 16.

Still referring to FIG. 2, the first pole 12 and second pole 14 of the electrical contact means 10 are attached to the inside face 28 of the first layer 30. The first pole 12 and second pole 14 are in direct, intimate electrical contact with the first face 32 of the electrically conductive interconnecting means 16. The electrically isolated conductive paths 18 are shown as columns of aligned conductive particles extending between the first face 32 and second face 34 of the electrically conductive interconnecting means 16. The second face 34 of the electrically conductive interconnecting means is in direct and intimate electrical contact with the electrically resistive material 20 which is attached to the inside face 36 of the second layer 38. The electrical contact means 10, the electrically conductive interconnecting means 16 and the electrically resistive material 20 form the sensing surface area 48. The sensing surface area 48 can be of varying size in relationship to the surface area of the insole 40. As the sensing surface area 48 of the insole 40 increases, the surface area of the electrically conductive interconnecting means 16 increases and, therefore, the number of electrically isolated conductive paths 18 increases. The electrically conductive interconnecting means 16 utilized in the preferred embodiment is an Electrically Conductive Polymer Interconnect (ECPI) supplied by AT&T. The ECPI is used to reduce shear and hysteresis effects. Accordingly, the foot force sensor 50 reduces shear and hysteresis effects by at least about 20%.

FIG. 3 is a partial, representative, exploded view of the foot force sensor 50. The first layer 30 and second layer 38 of the insole 40 are formed so as to approximate the dimensions of regular shoes with heel, arch and toe sections to allow for easy insertion into regular shoes. Since they are composed of a relatively thin, planar, flexible, resilient, dielectric material such as polyester sheet, they can be economically manufactured to fit different shoe sizes. The second layer 38 is shown with the electrically resistive material 20 adhered to its inside face 36. In the preferred embodiment the electrically resistive material 20 is a carbon ink which is coated on the inside face 36 of the second layer 38 in areas aligned, and coextensive, with the second face 34 of the electrically conductive interconnecting means 16. The electrically conductive interconnecting means 16 contains a plurality of electrically isolated conductive paths 18 of varying density and quantity which are laterally displaced from one another. In the event an insulating or spacing layer is placed between the first layer 30 and the second layer 38, it is not necessary that the electrically resistive material 20 be limited to the size of the second face 34 of the electrically conductive interconnecting means 16 provided the second face 34 is in total contact with the electrically resistive material 20. The electrically conductive interconnecting means 16 provides electrical connection between the first pole 12 of the electrical contact means 10 on the inside face 28 of the first layer 30 and the electrically resistive material 20 on the inside face 36 of the second layer 38. It also provides electrical connection between the electrically resistive material 20 and the second pole 14 of the electrical contact means 10. In the preferred embodiment the first pole 12 and second pole 14 of the electrical contact means 10 are a plurality of interdigitating fingers of which two each are shown in FIG. 3. The first pole 12 and second pole 14 are positioned on the inside face 28 of the first layer 30 to align with the electrically conductive interconnecting means 16. Electrical leads 22, 24 extend from the first pole 12 and second pole 14, respectively, and are attached to the inside face 28 of the first layer 30. A connector tab 42 extends outwardly from the insole 40. The electrical leads 22, 24 continue from the insole 40 on the connector tab 42. The electrical leads 22, 24 connect to the terminal connector 26.

Although different conductive inks may be used, in the preferred embodiment the electrical contact means 10 is a conductive silver ink printed on the inside face 28 of the second layer 38. The conductive silver ink can be of varying trace width and resistivity but in the preferred embodiment it has a trace width of not greater than about 0.02 inches and a resistivity of less than about 0.02 ohms per square per 25 microns. The interdigitating fingers comprising the first pole 12 and the second pole 14 can be of varying spacing but in the preferred embodiment they have a spacing of not greater than about 0.04 inches. The "pitch" defined as the sum of the width of the conductive silver ink trace and the spacing is therefore not greater than about 0.06 inches in the preferred embodiment.

The first layer 30 with the electrical contact means 10 attached to its inside face 28, the electrically conductive interconnecting means 16 and the second layer 38 with the electrically resistive material 20 attached to its inside face 36 are assembled such that the inside face 28 of the first layer 30 is juxtaposed with the inside face 36 of the second layer 38. The first layer 30 and the second layer 38 are adhered together using a suitable adhesive such as a heat cured, laminating polyester adhesive. The thickness of the assembled layers is not greater than about 0.025 inches.

Referring now to FIG. 4, the insole 40 having first layer 30 and second layer 38 is shown in a shoe ("S"). The connector tab 42 extends out of and above the shoe ("S") to facilitate the connection of the terminal connector 26 to an external signal transmission system. The connector tab 42 may be of integral construction with one or more of the layers of the insole 40.

Figure 5:
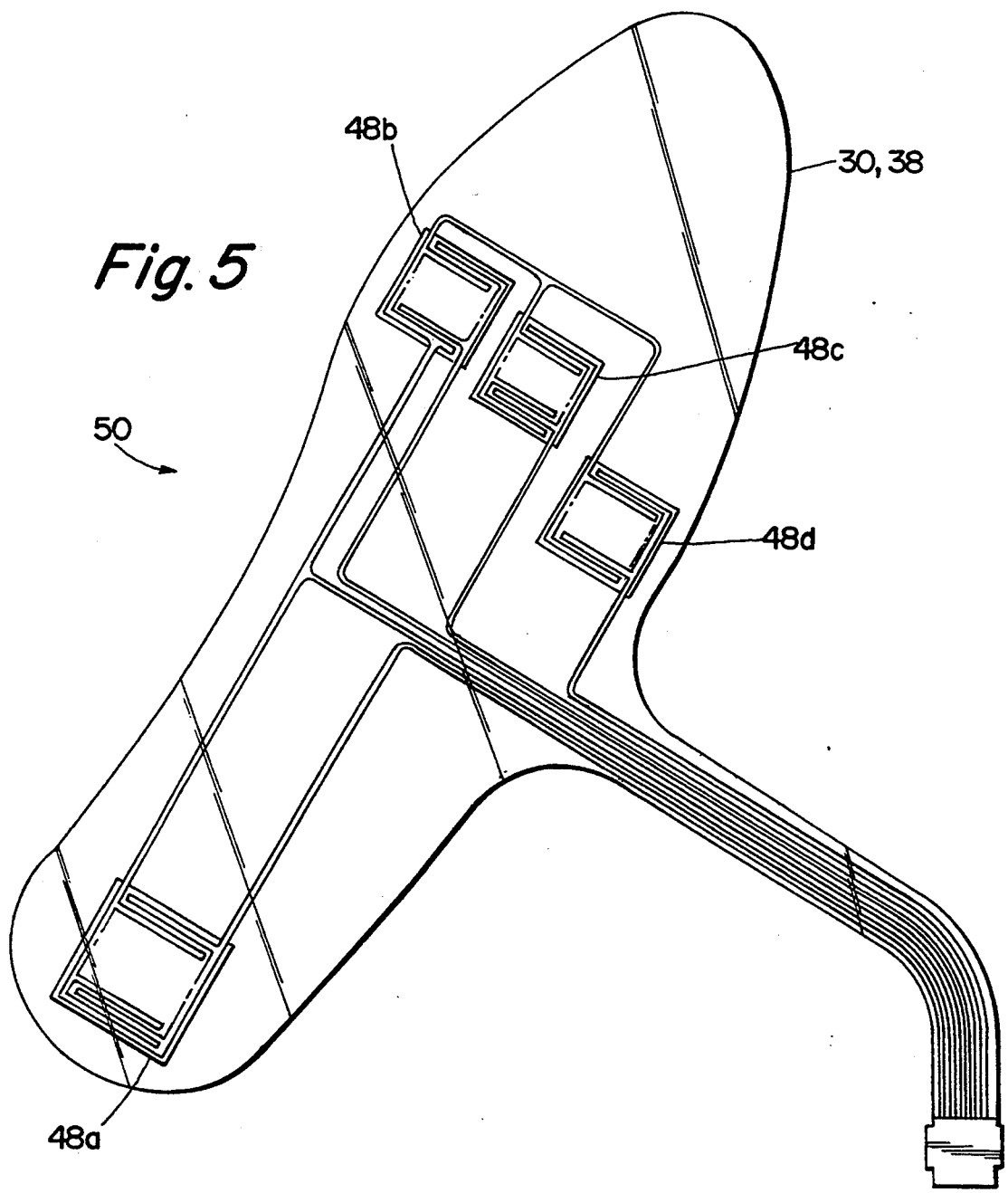
FIG. 5 is a plan view of a foot force sensor.

FIG. 5 is a plan view of the foot force sensor 50 showing the preferred embodiment. The sensing surface area 48 may be of varying size and may be separated into individual sensing surface areas. In the preferred embodiment four sensing surface areas 48a, 48b, 48c, and 48d are positioned on the foot force sensor 50. One sensing surface area is located at the area of the heel 48a. This sensing surface area has a surface area of about one square inch. Three other sensing surface areas are located at the areas of the first metatarsal head 48b, the second metatarsal head 48c and the fifth metatarsal head 48d, respectively. These three metatarsal sensing surface areas have a surface area of about 0.8 square inches each.

While there has been shown and described a preferred embodiment of the present invention, it is understood that the same is not limited thereto but is susceptible to numerous changes and modifications as known to those skilled in the art, therefore the invention is not to be limited to the details shown and described herein, but it is intended to cover all such changes and modifications as are encompassed by the scope of the appended claims.

What is claimed is:

1. A foot force sensor, comprising:
    (a) an insole having a plurality of layers of relatively thin, planar, flexible, resilient, dielectric material; and
    (b) electrical contact means attached to said insole said electrical contact means having first and second poles defining an open circuit configuration and electrical leads extending from said first and second poles; and
    (c) electrically resistive material applied to said insole such that said electrically resistive material is displaced from said electrical contact means; and
    (d) electrically conductive interconnecting means having first and second faces, said first face electrically connected to said electrical contact means and said second face electrically connected said electrically resistive material, said electrically conductive interconnecting means having a plurality of electrically isolated conductive paths laterally displaced from one another and extending from said first face to said second face, said electrically conductive interconnecting means having an electrical resistance which decreases as a compressive force applied to said first or second face increases whereby a closed electrical circuit with resistance varying with the amount of compressive force applied to said insole is established between said first pole and said second pole of said electrical contact means through said electrically conductive interconnecting means and said electrically resistive material.

2. The foot force sensor of claim 1 wherein said first and second poles of said electrical contact means are a plurality of interdigitating conductive fingers.

3. The foot force sensor of claim 1 wherein said electrical contact means is conductive ink applied to said insole.

4. The foot force sensor of claim 3 wherein said conductive ink is silver conductive ink.

5. The foot force sensor of claim 3 wherein said conductive ink has a resistivity of less than about 0.02 ohms per square per 25 micron.

6. The foot force sensor of claim 3 wherein said conductive ink has a width of not greater than about 0.02 inches.

7. The foot force sensor of claim 1 wherein said electrically resistive material is carbon ink applied to said insole.

8. The foot force sensor of claim 1 wherein said dielectric material is a polyester material.

9. The foot force sensor of claim 1 wherein said electrical contact means, said electrically resistive material and said electrically conductive interconnecting means are positioned on said insole to align with the heel, and 1st, 2nd, and 5th metatarsal heads of a human foot.

10. A foot force sensor, comprising:
    (a) an insole having first and second layers, said layers composed of relatively thin, flexible, planar, resilient dielectric material, said layers juxtaposed to one another in a face-to-face stacked relationship; and
    (b) an electrically resistive material interposed between said first and second layers; and
    (c) electrical contact means interposed between said first and second layers such that said electrical contact means is displaced from said electrically resistive material, said electrical contact means having first and second poles defining an open circuit configuration and electrical leads extending from said first and second poles; and
    (d) electrically conductive interconnecting means having first and second faces interposed between said first and second layers, said first face electrically connected to said electrical contact means and said second face electrically connected to said electrically resistive material, said electrically conductive interconnecting means having a plurality of electrically isolated conductive paths laterally displaced from one another and extending from said first face to said second face, said electrically conductive interconnecting means having an electrical resistance which decreases as a compressive force applied to said first or second face increases such that a closed electrical circuit with resistance varying with the amount of compressive force applied to said insole is established between said first pole and said second pole of said electrical contact means through said electrically conductive interconnecting means and said electrically resistive material.

11. The foot force sensor of claim 10 wherein said first and second poles of said electrical contact means are a plurality of interdigitating conductive fingers.

12. The foot force sensor of claim 10 wherein said electrical contact means is conductive ink applied to said insole.

13. The foot force sensor of claim 12 wherein said conductive ink is silver conductive ink.

14. The foot force sensor of claim 12 wherein said conductive ink has a resistivity of less than about 0.02 ohms per square per 25 microns.

15. The foot force sensor of claim 12 wherein said conductive ink has a width of not greater than about 0.02 inches.

16. The foot force sensor of claim 10 wherein said electrically resistive material is carbon ink applied to said insole.

17. The foot force sensor of claim 10 wherein said dielectric material is polyester.

18. The foot force sensor of claim 12 wherein said electrical contact means, electrically resistive material and said electrically conductive interconnecting means are positioned on said insole to align with the heel, and 1st, 2nd and 5th metatarsal heads of a human foot.

* * * * *